United States Patent
Inomata

(10) Patent No.: US 11,234,664 B2
(45) Date of Patent: Feb. 1, 2022

(54) X-RAY FLUOROSCOPIC IMAGING APPARATUS

(71) Applicant: SHIMADZU CORPORATION, Kyoto (JP)

(72) Inventor: Shuichi Inomata, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 105 days.

(21) Appl. No.: 16/670,028

(22) Filed: Oct. 31, 2019

(65) Prior Publication Data

US 2021/0038179 A1    Feb. 11, 2021

(30) Foreign Application Priority Data

Aug. 9, 2019  (JP) .............................. JP2019-147020

(51) Int. Cl.
*A61B 6/00* (2006.01)
*G01N 23/04* (2018.01)

(52) U.S. Cl.
CPC .............. *A61B 6/487* (2013.01); *A61B 6/467* (2013.01); *A61B 6/461* (2013.01); *G01N 23/043* (2013.01); *G01N 2223/406* (2013.01)

(58) Field of Classification Search
CPC ...... A61B 6/467; A61B 6/487; G01N 23/043; G01N 2223/406
See application file for complete search history.

(56) References Cited

U.S. PATENT DOCUMENTS

| | | | | |
|---|---|---|---|---|
| 3,491,239 A * | 1/1970 | Dalman | H04N 5/32 378/97 |
| 5,404,485 A * | 4/1995 | Ban | G06F 3/0601 711/202 |
| 5,636,259 A * | 6/1997 | Khutoryansky | A61B 6/0487 378/197 |
| 6,609,826 B1 * | 8/2003 | Fujii | A61B 6/12 378/197 |
| 2002/0172498 A1 * | 11/2002 | Esenyan | H04N 5/9201 386/241 |
| 2012/0027178 A1 * | 2/2012 | Mabini | A61B 6/487 378/98 |

FOREIGN PATENT DOCUMENTS

JP    2016-022248 A    2/2016

* cited by examiner

*Primary Examiner* — Chih-Cheng Kao
(74) *Attorney, Agent, or Firm* — Andrew F. Young, Esq.; Nolte Lackenbach Siegel

(57) ABSTRACT

An X-ray fluoroscopic imaging apparatus includes a fluoroscopic recording button that an operator operates to record a fluoroscopic image as a still image or a moving image in a storage during fluoroscopic imaging and record, as the still image or the moving image in the storage, the fluoroscopic image recorded in a temporary storage after completion of the fluoroscopic imaging.

8 Claims, 8 Drawing Sheets

FIG.7A

RECORDING POSITION:   | SECOND HALF ▽ |
                      | MIDDLE        |
                      | FIRST HALF    |

RECORDING LENGTH:     | 10 sec |

FIG.7B

EXAMINATION TYPE:     | SWALLOWING |
                      | HEART      |
                      | :          |
                      | :          |

X-RAY FLUOROSCOPIC IMAGING APPARATUS

CROSS-REFERENCE TO RELATED APPLICATIONS

This application claims the benefit of priority to Japanese Patent Application No. 2019-147020 filed on Aug. 9, 2019, the entire contents of which are hereby incorporated herein by reference.

BACKGROUND OF THE INVENTION

Field of the Invention

The present invention relates to an X-ray fluoroscopic imaging apparatus.

Description of the Background Art

Conventionally, an X-ray fluoroscopic imaging apparatus that performs fluoroscopic imaging of a subject with X-rays is known. Such an X-ray fluoroscopic imaging apparatus is disclosed in Japanese Patent Laid-Open No. 2016-022248, for example.

Japanese Patent Laid-Open No. 2016-022248 discloses an X-ray fluoroscopic imaging apparatus that performs fluoroscopic imaging of a subject with X-rays. This X-ray fluoroscopic imaging apparatus includes a fluoroscopic foot switch. In this X-ray fluoroscopic imaging apparatus, fluoroscopic imaging is continued while the fluoroscopic foot switch is depressed, and fluoroscopic images collected at a predetermined frame rate are displayed as a moving image on a display. The X-ray fluoroscopic imaging apparatus has a function (so-called last image hold function) of acquiring and holding an image of the final frame among the fluoroscopic images collected by fluoroscopic imaging.

However, in the X-ray fluoroscopic imaging apparatus disclosed in Japanese Patent Laid-Open No. 2016-022248, using the last image hold function, only the image of the final frame among the fluoroscopic images collected by fluoroscopic imaging can be recorded, and the fluoroscopic images other than the image of the final frame cannot be recorded. That is, the degree of freedom of recording fluoroscopic images is low, and thus a user's desire to record arbitrary fluoroscopic images for diagnosis, for example, cannot be sufficiently met. In this regard, there is room for improvement in the X-ray fluoroscopic imaging apparatus disclosed in Japanese Patent Laid-Open No. 2016-022248.

SUMMARY OF THE INVENTION

The present invention is intended to solve the above problem. The present invention aims to provide an X-ray fluoroscopic imaging apparatus capable of sufficiently meeting a user's desire to record arbitrary fluoroscopic images by improving the degree of freedom of recording fluoroscopic images.

In order to attain the aforementioned object, an X-ray fluoroscopic imaging apparatus according to an aspect of the present invention includes an imager configured to perform fluoroscopic imaging of a subject with X-rays, a temporary storage configured to temporarily record a fluoroscopic image acquired by the imager, a storage configured to record, as a still image or a moving image, the fluoroscopic image recorded in the temporary storage, and a fluoroscopic recording button that an operator operates to record the fluoroscopic image as the still image or the moving image in the storage during the fluoroscopic imaging and record, as the still image or the moving image in the storage, the fluoroscopic image recorded in the temporary storage after completion of the fluoroscopic imaging.

According to the present invention, the fluoroscopic recording button is provided for the operator to record the fluoroscopic image as the still image or the moving image in the storage during the fluoroscopic imaging and record, as the still image or the moving image in the storage, the fluoroscopic image recorded in the temporary storage after the completion of the fluoroscopic imaging. Accordingly, the fluoroscopic image can be recorded as the still image or the moving image in the storage both during the fluoroscopic imaging and after the completion of the fluoroscopic imaging by operating the fluoroscopic recording button. Consequently, a user (operator) can record a desired (arbitrary) fluoroscopic image in a desired format (a still image or a moving image) in the storage at the desired timing (during the fluoroscopic imaging or after the completion of the fluoroscopic imaging). Thus, the degree of freedom of recording the fluoroscopic image can be improved, and thus it is possible to provide the X-ray fluoroscopic imaging apparatus capable of sufficiently meeting a user's desire to record an arbitrary fluoroscopic image for diagnosis, for example.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 7A is a diagram for illustrating a first example of setting of a recording range at the time of recording fluoroscopic images as a moving image after completion of fluoroscopic imaging in an X-ray fluoroscopic imaging apparatus according to an embodiment.

FIG. 7B is a diagram for illustrating a second example of setting of a recording range at the time of recording fluoroscopic images as a moving image after completion of fluoroscopic imaging in an X-ray fluoroscopic imaging apparatus according to an embodiment.

DESCRIPTION OF THE PREFERRED EMBODIMENTS

Embodiments of the present invention are hereinafter described with reference to the drawings.

(Configuration of X-Ray Fluoroscopic Imaging Apparatus)

The configuration of an X-ray fluoroscopic imaging apparatus 100 according to embodiments is now described with reference to FIGS. 1 to 8.

Figure 1:
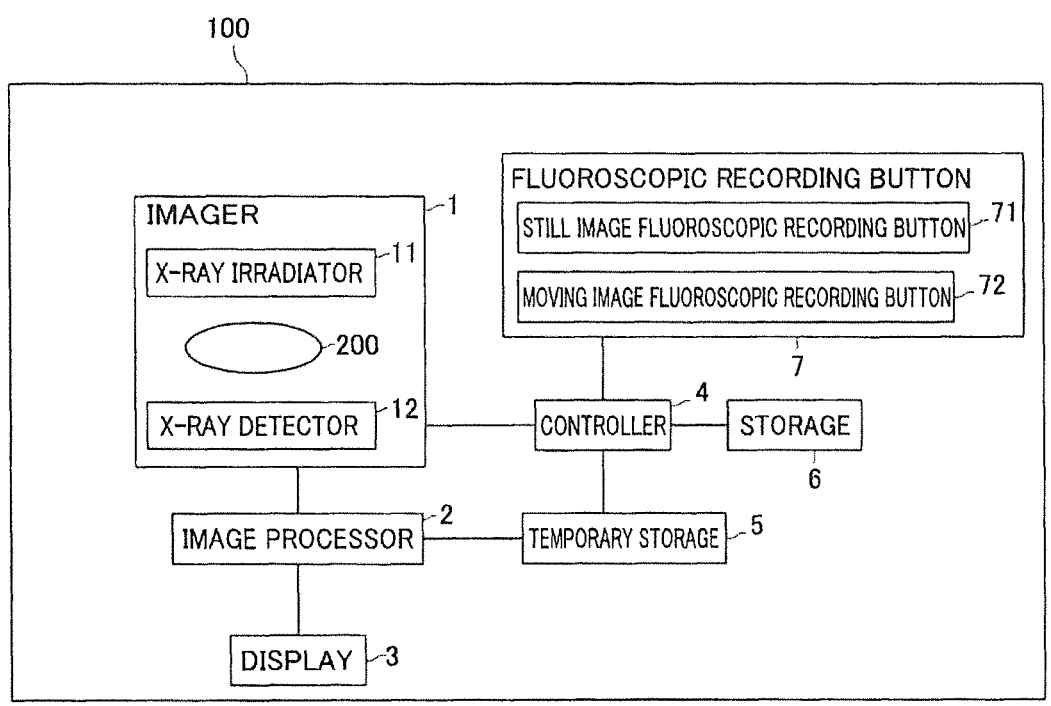
FIG. 1 is a block diagram showing the configuration of an X-ray fluoroscopic imaging apparatus according to an embodiment.

As shown in FIG. 1, the X-ray fluoroscopic imaging apparatus 100 is an apparatus (so-called X-ray television apparatus) that performs fluoroscopic imaging of a human subject 200 with X-rays. The X-ray fluoroscopic imaging apparatus 100 is configured to be able to generate a fluoroscopic image 201 (see FIG. 2) of the inside of the subject 200 in real time based on the result of fluoroscopic imaging of the subject 200 with X-rays.

The X-ray fluoroscopic imaging apparatus 100 includes an imager 1 that images the subject 200 to be imaged (to be examined) with X-rays. The imager 1 includes an X-ray irradiator 11 and an X-ray detector 12. The X-ray irradiator 11 generates X-rays and irradiates the subject 200 with the X-rays. The X-ray irradiator 11 includes an X-ray tube as an X-ray source and a collimator that adjusts the irradiation range of the X-rays generated by the X-ray tube, for example. The X-ray detector 12 detects the X-rays emitted from the X-ray irradiator 11 and transmitted through the subject 200. The X-ray detector 12 includes a flat panel detector (FPD), for example. The X-ray detector 12 transmits detection signals, which are electrical signals corresponding to the detected X-rays, to an image processor 2 described below. The X-ray irradiator 11 and the X-ray detector 12 face each other with the subject 200 interposed therebetween. The X-ray fluoroscopic imaging apparatus 100 may include a table on which the subject 200 is placed. In this case, the X-ray irradiator 11 and the X-ray detector 12 face each other with the table interposed therebetween.

The X-ray fluoroscopic imaging apparatus 100 includes the image processor 2 that generates the fluoroscopic image 201 of the inside of the subject 200 based on the detection signals from the X-ray detector 12 of the imager 1. The image processor 2 includes a processor such as a GPU and a memory that stores information, for example. The image processor 2 is configured to generate the fluoroscopic image 201 of the inside of the subject 200 at a predetermined frame rate (about several frames to several tens of frames per second, for example). The X-ray fluoroscopic imaging apparatus 100 includes a display 3 that displays the fluoroscopic image 201 of the inside of the subject 200 generated by the image processor 2. The display 3 includes a liquid crystal monitor capable of displaying information, for example. On the display 3, fluoroscopic images 201 generated at the predetermined frame rate are displayed in real time as a moving image, for example. The X-ray fluoroscopic imaging apparatus 100 includes a controller 4 that controls the operation of the X-ray fluoroscopic imaging apparatus 100. The controller 4 includes a processor such as a CPU and a memory that stores information.

The X-ray fluoroscopic imaging apparatus 100 also includes a temporary storage 5 that temporarily records the fluoroscopic images 201 acquired by the imager 1. The temporary storage 5 includes a volatile memory such as a RAM, and is configured to temporarily store input information. As the temporary storage 5, the volatile memory of the image processor 2 or the volatile memory of the controller 4 can be used, for example. The fluoroscopic images 201 generated at the predetermined frame rate are recorded in the temporary storage 5. The fluoroscopic images 201 recorded in the temporary storage 5 include a plurality of frames of images recorded from the start of recording of the fluoroscopic image 201 to the temporary storage 5 until the end of the recording. The start and end of recording of the fluoroscopic images 201 to the temporary storage 5 can be set at timing synchronized with the start and end of fluoroscopic imaging, for example. The X-ray fluoroscopic imaging apparatus 100 further includes a storage 6 that records, as a still image or a moving image, the fluoroscopic images 201 recorded in the temporary storage 5. The storage 6 includes a nonvolatile memory such as an HDD, and is configured to store input information.

In embodiments, the X-ray fluoroscopic imaging apparatus 100 includes a fluoroscopic recording button 7 that an operator (user) operates to record the fluoroscopic images 201 as a still image or a moving image in the storage 6 during fluoroscopic imaging and to record, as a still image or a moving image in the storage 6, the fluoroscopic images 201 recorded in the temporary storage 5 after completion of fluoroscopic imaging. The fluoroscopic recording button 7 includes two buttons, a still image fluoroscopic recording button 71 that the operator operates to record the fluoroscopic image 201 as a still image in the storage 6 and a moving image fluoroscopic recording button 72 that the operator operates to record the fluoroscopic images 201 as a moving image in the storage 6. Both the still image fluoroscopic recording button 71 and the moving image fluoroscopic recording button 72 are push-button type switches.

(Recording of Fluoroscopic Image)

Figure 2:
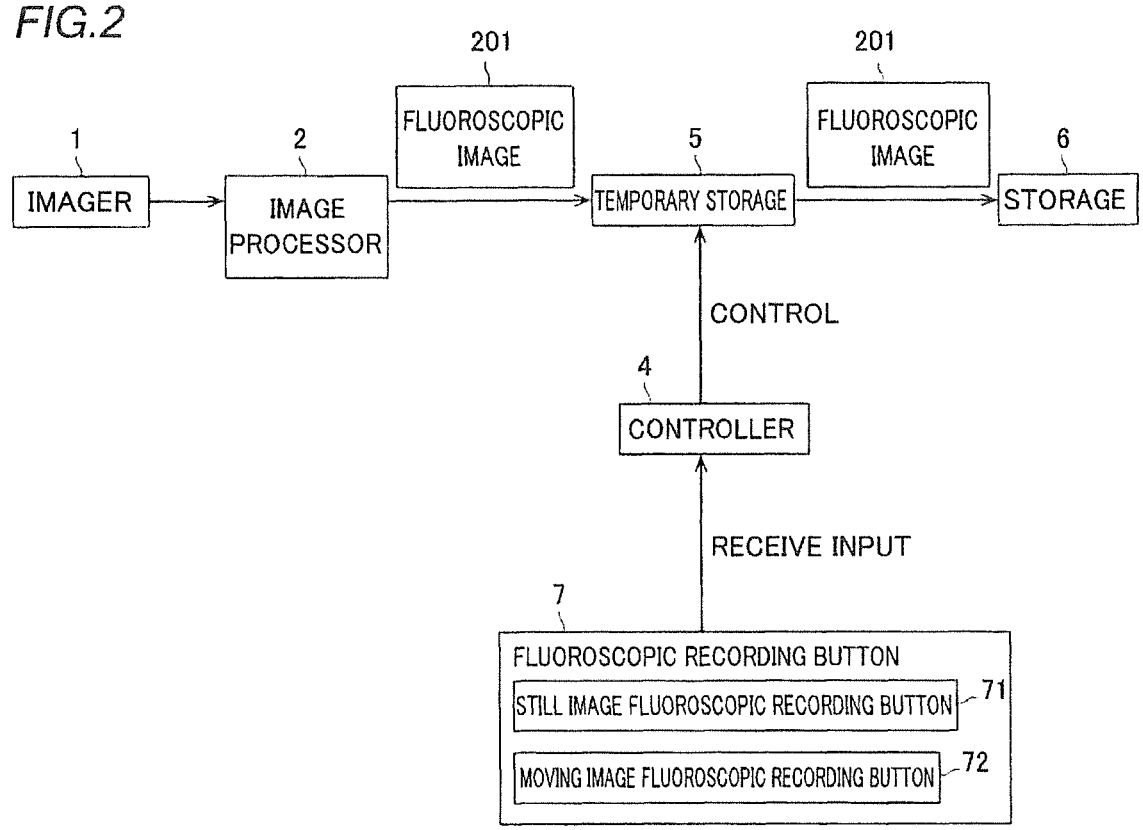
FIG. 2 is a diagram for illustrating recording of a fluoroscopic image in a storage of an X-ray fluoroscopic imaging apparatus according to an embodiment.

As shown in FIG. 2, the controller 4 is configured or programmed to perform control to record the fluoroscopic images 201 as a still image or a moving image in the storage 6 in accordance with operation of the fluoroscopic recording button 7 when the operator such as a technician operates the fluoroscopic recording button 7 during fluoroscopic imaging. Specifically, the controller 4 is configured or programmed to perform control to record the fluoroscopic image 201 as a still image in the storage 6 when the operator operates the still image fluoroscopic recording button 71 of the fluoroscopic recording button 7 during fluoroscopic imaging. Furthermore, the controller 4 is configured or programmed to perform control to record the fluoroscopic images 201 as a moving image in the storage 6 when the operator operates the moving image fluoroscopic recording button 72 of the fluoroscopic recording button 7 during fluoroscopic imaging.

Similarly, the controller 4 is configured or programmed to perform control to record, as a still image or a moving image in the storage 6, the fluoroscopic images 201 recorded in the temporary storage 5 in accordance with the operation of the fluoroscopic recording button 7 when the operator operates the fluoroscopic recording button 7 after completion of fluoroscopic imaging. Specifically, the controller 4 is configured or programmed to perform control to record, as a still image in the storage 6, the fluoroscopic image 201 recorded in the temporary storage 5 when the operator operates the still image fluoroscopic recording button 71 of the fluoroscopic recording button 7 after completion of fluoroscopic imaging. Furthermore, the controller 4 is configured or programmed to perform control to record, as a moving image in the storage 6, the fluoroscopic images 201 recorded in the temporary storage 5 when the operator operates the moving image fluoroscopic recording button 72 of the fluoroscopic recording button 7 after completion of fluoroscopic imaging.

Unlike the fluoroscopic images 201 temporarily recorded in the temporary storage 5, the fluoroscopic images 201 recorded in the storage 6 can be stored for a long period of time, and thus the same can be used subsequently. As a mode of subsequent use of the fluoroscopic images 201 recorded in the storage 6, there may be a mode of use at the time of diagnosis in an examination using the fluoroscopic images 201 for diagnosis, for example. Examples of the examination using the fluoroscopic images 201 for diagnosis include a swallowing examination and an examination for a newborn, for example. For example, the fluoroscopic images 201 as a moving image of about ten seconds can be used at the time of diagnosis in the swallowing examination. Furthermore, the fluoroscopic image 201 as a still image can be used at the time of diagnosis in the examination for a newborn. The fluoroscopic images 201 recorded in the storage 6 can be used as a record of the basis for such diagnosis, for example.

<Recording of Fluoroscopic Image During Fluoroscopic Imaging>

Recording of the fluoroscopic images 201 during fluoroscopic imaging is now described with reference to FIGS. 3 and 4.

Figure 3:
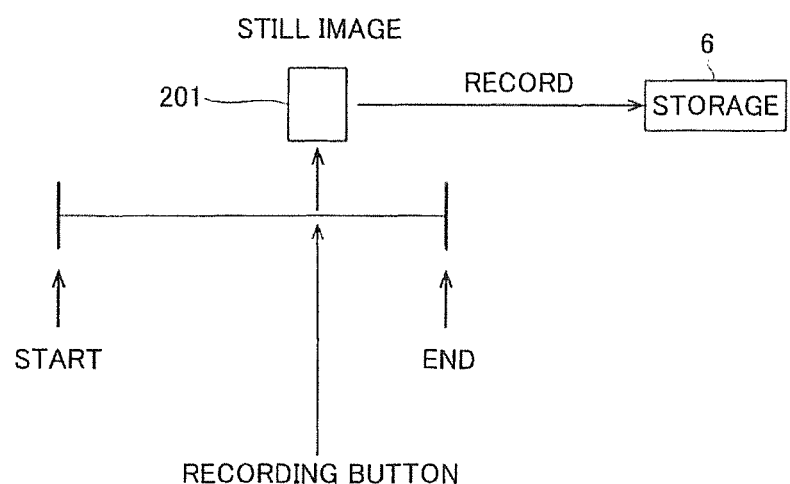
FIG. 3 is a diagram for illustrating recording of a fluoroscopic image as a still image during fluoroscopic imaging in an X-ray fluoroscopic imaging apparatus according to an embodiment.

As shown in FIG. 3, the controller 4 is configured to perform control to record the fluoroscopic image 201 being displayed on the display 3 (see FIG. 1) as a still image in the storage 6 when the still image fluoroscopic recording button 71 of the fluoroscopic recording button 7 (see FIG. 1) is operated by the operator while the fluoroscopic image 201 acquired by the imager 1 is displayed on the display 3 in real time during fluoroscopic imaging. At this time, the fluoroscopic image 201 recorded in the temporary storage 5 (see FIG. 1) may be recorded in the storage 6, or the fluoroscopic image 201 generated by the image processor 2 may be recorded in the storage 6 without passing through the temporary storage 5.

During fluoroscopic imaging, the operator presses the still image fluoroscopic recording button 71 of the fluoroscopic recording button 7 only once at the timing when the fluoroscopic image 201 desired to be recorded as a still image is displayed on the display 3 while visually confirming the fluoroscopic image 201 being displayed on the display 3. Consequently, one frame of the fluoroscopic image 201 being displayed on the display 3 is recorded as a still image in the storage 6 at the timing when the operator presses the still image fluoroscopic recording button 71 of the fluoroscopic recording button 7.

Figure 4:
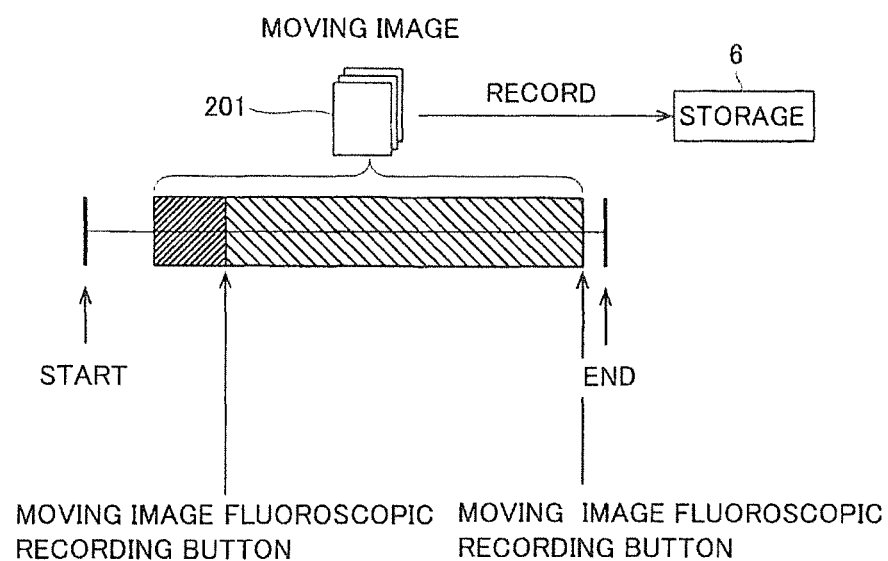
FIG. 4 is a diagram for illustrating recording of fluoroscopic images as a moving image during fluoroscopic imaging in an X-ray fluoroscopic imaging apparatus according to an embodiment.

As shown in FIG. 4, the controller 4 is configured to perform control to record the fluoroscopic images 201 being displayed on the display 3 (see FIG. 1) as a moving image in the storage 6 when the moving image fluoroscopic recording button 72 of the fluoroscopic recording button 7 (see FIG. 1) is operated by the operator while the fluoroscopic images 201 acquired by the imager 1 are displayed on the display 3 in real time during fluoroscopic imaging. At this time, the fluoroscopic images 201 recorded in the temporary storage 5 (see FIG. 1) may be recorded in the storage 6, or the fluoroscopic images 201 generated by the image processor 2 may be stored in the storage 6 without passing through the temporary storage 5.

During fluoroscopic imaging, the operator presses the moving image fluoroscopic recording button 72 of the fluoroscopic recording button 7 only once at the timing when the fluoroscopic images 201 desired to be recorded as a moving image are displayed on the display 3 while visually confirming the fluoroscopic images 201 being displayed on the display 3. This operation is a moving image fluoroscopic recording start operation during fluoroscopic imaging. Consequently, recording of the fluoroscopic images 201 as a moving image in the storage 6 is started from the fluoroscopic images 201 being displayed on the display 3 at the timing when the operator presses the moving image fluoroscopic recording button 72 of the fluoroscopic recording button 7. Then, the operator presses the moving image fluoroscopic recording button 72 of the fluoroscopic recording button 7 only once at the timing when the operator desires to end the recording of the fluoroscopic images 201 as a moving image in the storage 6. This operation is a moving image fluoroscopic recording end operation during fluoroscopic imaging. Consequently, the recording of the fluoroscopic images 201 as a moving image in the storage 6 is ended. As a result, the fluoroscopic images 201 including the plurality of frames of images displayed on the display 3 between the moving image fluoroscopic recording start operation and the moving image fluoroscopic recording end operation are recorded as a moving image in the storage 6.

When the fluoroscopic images 201 are recorded as a moving image in the storage 6 during fluoroscopic imaging, the X-ray fluoroscopic imaging apparatus 100 may go back in time by a certain time (several seconds, for example) from a time point at which the moving image fluoroscopic recording start operation is performed, and start to record the fluoroscopic images 201 in the storage 6. Thus, it is possible to significantly reduce or prevent the occurrence of recording omission (the likelihood that the fluoroscopic images 201 to be recorded are not recorded) depending on the timing when the moving image fluoroscopic recording start operation is performed.

<Recording of Fluoroscopic Image after Completion of Fluoroscopic Imaging>

Recording of the fluoroscopic image 201 after completion of fluoroscopic imaging is now described with reference to FIGS. 5 to 7.

Figure 5:
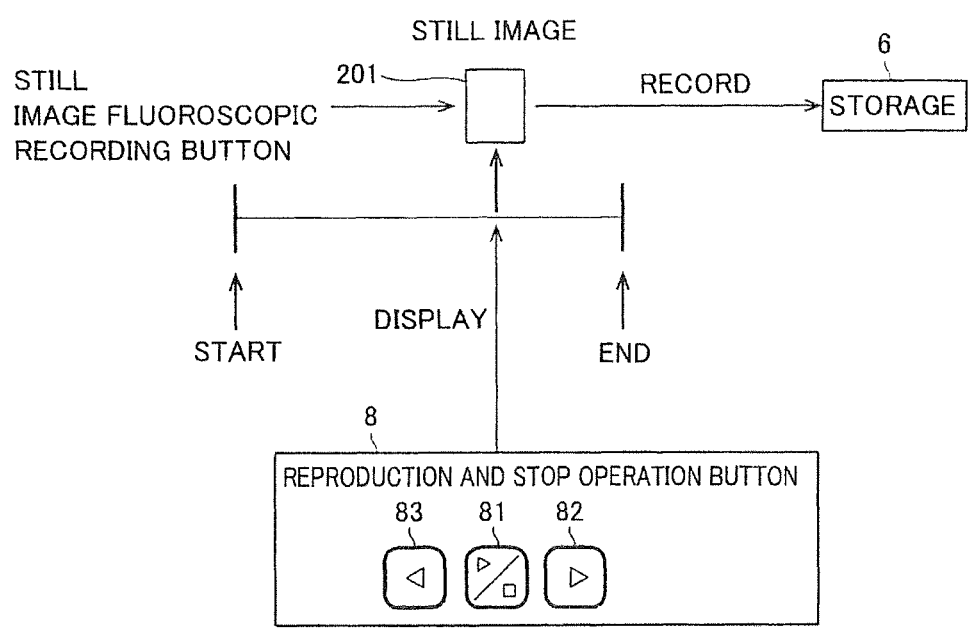
FIG. 5 is a diagram for illustrating recording of a fluoroscopic image as a still image after completion of fluoroscopic imaging in an X-ray fluoroscopic imaging apparatus according to an embodiment.

As shown in FIG. 5, the controller 4 is configured or programmed to perform control to record an arbitrary fluoroscopic image 201 being displayed on the display 3 (see FIG. 1) as a still image in the storage 6 when the still image fluoroscopic recording button 71 of the fluoroscopic recording button 7 (see FIG. 1) is operated by the operator while the arbitrary fluoroscopic image 201 among the fluoroscopic images 201 recorded in the temporary storage 5 (see FIG. 1) is displayed on the display 3 after completion of fluoroscopic imaging.

Specifically, the X-ray fluoroscopic imaging apparatus 100 further includes a reproduction and stop operation button 8 that the operator operates to reproduce or stop reproducing the fluoroscopic images 201 recorded in the temporary storage 5 on the display 3 after competition of fluoroscopic imaging. The reproduction and stop operation button 8 includes a reproduction and stop button 81 that the operator operates to reproduce the fluoroscopic images 201 as a moving image and stop reproduction of the fluoroscopic images 201 as a moving image being reproduced, a forward button 82 that the operator operates to set forward a reproduction position of the fluoroscopic images 201 as a moving image in terms of time, and a backward button 83 that the operator operates to set back the reproduction position of the fluoroscopic images 201 as a moving image in terms of time. The reproduction and stop button 81, the forward button 82, and the backward button 83 are all push-button type switches.

The controller 4 is configured or programmed to perform control to record an arbitrary fluoroscopic image 201 being displayed on the display 3 as a still image in the storage 6 when the still image fluoroscopic recording button 71 of the fluoroscopic recording button 7 is operated while the arbitrary fluoroscopic image 201 is displayed on the display 3 by operation of the reproduction and stop operation button 8 by the operator after completion of fluoroscopic imaging.

The operator performs an operation for displaying the fluoroscopic images 201 recorded in the temporary storage 5 on the display 3 after completion of fluoroscopic imaging and before discarding of the fluoroscopic images 201 recorded in the temporary storage 5. Then, the operator performs an operation for displaying the fluoroscopic image 201 desired to be recorded as a still image on the display 3 using the reproduction and stop button 81, the forward button 82, and the backward button 83 of the reproduction and stop operation button 8 as appropriate while visually confirming the fluoroscopic image 201 being displayed on the display 3. Then, the operator presses the still image fluoroscopic recording button 71 of the fluoroscopic recording button 7 only once in a state in which the fluoroscopic image 201 desired to be recorded as a still image is displayed on the display 3. Consequently, one frame of the fluoroscopic image 201 being displayed on the display 3 is recorded as a still image in the storage 6 at the timing when the operator presses the still image fluoroscopic recording button 71 of the fluoroscopic recording button 7.

Figure 6:
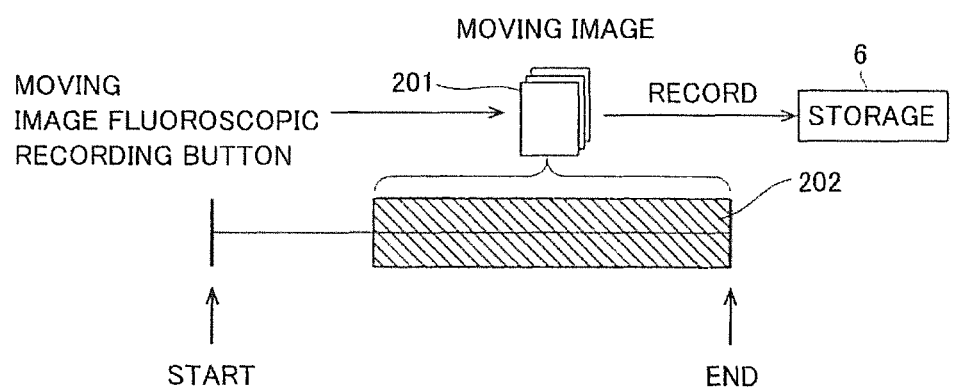
FIG. 6 is a diagram for illustrating recording of fluoroscopic images as a moving image after completion of fluoroscopic imaging in an X-ray fluoroscopic imaging apparatus according to an embodiment.

As shown in FIG. 6, the controller 4 is configured or programmed to perform control to record, as a moving image in the storage 6, images in a predetermined range 202 among the fluoroscopic images 201 recorded in the temporary storage 5 (see FIG. 1) when the moving image fluoroscopic recording button 72 of the fluoroscopic recording button 7 (see FIG. 1) is operated by the operator after completion of fluoroscopic imaging.

The operator presses the moving image fluoroscopic recording button 72 of the fluoroscopic recording button 7 only once after completion of fluoroscopic imaging and before discarding of the fluoroscopic images 201 recorded in the temporary storage 5. Consequently, the fluoroscopic images 201 including a plurality of frames of images in the predetermined range 202 among the fluoroscopic images 201 recorded in the temporary storage 5 are recorded as a moving image in the storage 6. Although the range 202 is not particularly limited, in an example shown in FIG. 6, the range 202 is set as a range from a fluoroscopic imaging completion time point to a time point before a predetermined time.

The range 202, which is a recording range of the fluoroscopic images 201 as a moving image after completion of fluoroscopic imaging, may be a fixed range determined in advance in the X-ray fluoroscopic imaging apparatus 100, or a range based on user specification. When the range 202 is a range based on user specification, the recording position and the recording length can be directly specified as the range 202 by the user, for example, as shown in FIG. 7A. In this case, the recording position can be specified from a plurality of predetermined candidate positions such as "first half", "middle", and "second half", for example. Furthermore, the user can specify an arbitrary value (the number of seconds or the number of frames) as the recording length, for example.

When the range 202 is a range based on user specification, the recording position and the recording length can be indirectly specified as the range 202 by the user, for example, as shown in FIG. 7B. FIG. 7B shows an example in which the recording position and the recording length corresponding to the specified examination type are automatically set as the range 202 when the examination type is specified by the user. In this case, the examination type specified by the user can be specified from predetermined candidate types such as "swallowing" and "heart".

When the range 202 is a range based on user specification, the controller 4 performs control to display a setting screen of the range 202 on the display 3, as shown in FIGS. 7A and 7B, for example. The controller 4 performs control to set the recording position and recording length of the range 202 based on information specified by the user via the setting screen displayed on the display 3.

<Auto Fluoroscopic Recording Setting>

Figure 8A:
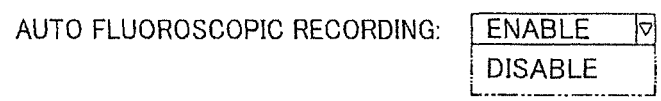
FIG. 8A is a diagram showing an example of auto recording setting in an X-ray fluoroscopic imaging apparatus according to an embodiment.

In an embodiment, as shown in FIG. 8A, the X-ray fluoroscopic imaging apparatus 100 is configured to switchably enable or disable auto fluoroscopic recording setting. The auto fluoroscopic recording setting is setting for automatically recording the fluoroscopic image 201 in the storage 6. That is, the auto fluoroscopic recording setting is setting for recording the fluoroscopic image 201 in the storage 6 regardless of the operation of the fluoroscopic recording button 7 (even when the fluoroscopic recording button 7 is not operated).

When the auto fluoroscopic recording setting is to be switched to be enabled or disabled, the controller 4 performs control to display a setting screen of the auto fluoroscopic recording setting on the display 3, as shown in FIG. 8A, for example. Then, the controller 4 performs control to switch the auto fluoroscopic recording setting to be enabled or disabled based on information specified by the user via the setting screen displayed on the display 3 and to set the auto fluoroscopic recording setting.

Figure 8B:
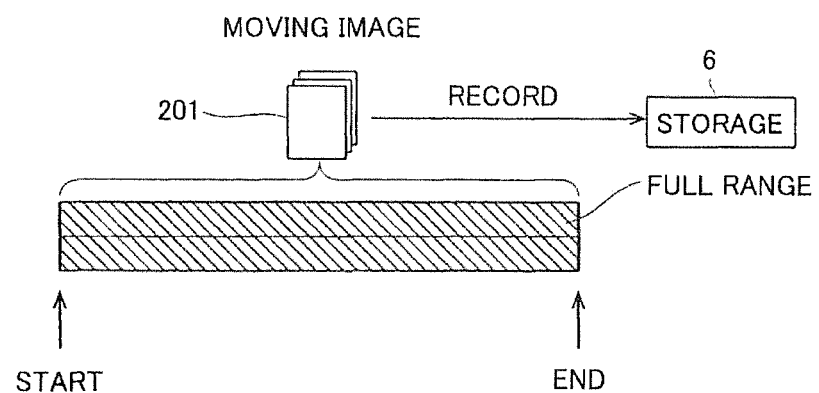
FIG. 8B is a diagram for illustrating recording of fluoroscopic images with auto recording setting enabled in an X-ray fluoroscopic imaging apparatus according to an embodiment.

The controller 4 is configured or programmed to perform control to record all of the fluoroscopic images 201 acquired by the imager 1 during fluoroscopic imaging in the storage 6 regardless of the operation of the fluoroscopic recording button 7 (even when the fluoroscopic recording button 7 is not operated) when the auto fluoroscopic recording setting is enabled, as shown in FIG. 8B. That is, the controller 4 is configured or programmed to perform control to record the fluoroscopic images 201 including all frames of images acquired by the imager 1 during fluoroscopic imaging as a moving image in the storage 6. On the other hand, the controller 4 does not perform control to automatically record the fluoroscopic images 201 in the storage 6 when the auto fluoroscopic recording setting is disabled. In this case, the operator operates the fluoroscopic recording button 7 as described above to record the fluoroscopic images 201 acquired by the imager 1 during fluoroscopic imaging in the storage 6.

Advantages of Embodiments

According to the various embodiments described above, the following advantages are obtained.

According to an embodiment, as described above, the X-ray fluoroscopic imaging apparatus 100 includes the fluoroscopic recording button 7 that the operator operates to record the fluoroscopic images 201 as a still image or a moving image in the storage 6 during fluoroscopic imaging and record, as a still image or a moving image in the storage 6, the fluoroscopic images 201 recorded in the temporary storage 5 after completion of fluoroscopic imaging. Accordingly, the fluoroscopic images 201 can be recorded as a still image or a moving image in the storage 6 both during fluoroscopic imaging and after completion of fluoroscopic imaging by operating the fluoroscopic recording button 7. Consequently, the user can record desired (arbitrary) fluoroscopic images 201 in a desired format (a still image or a moving image) in the storage 6 at the desired timing (during fluoroscopic imaging or after completion of fluoroscopic imaging). Thus, the degree of freedom of recording the fluoroscopic images 201 can be improved, and thus it is possible to provide the X-ray fluoroscopic imaging apparatus 100 capable of sufficiently meeting a user's desire to record arbitrary fluoroscopic images 201 for diagnosis, for example.

According to an embodiment, as described above, the X-ray fluoroscopic imaging apparatus 100 is configured to record the fluoroscopic images 201 as a still image or a moving image in the storage 6 in accordance with the operation of the fluoroscopic recording button 7 during fluoroscopic imaging, and record, as a still image or a moving image in the storage 6, the fluoroscopic images 201 recorded in the temporary storage 5 in accordance with the operation of the fluoroscopic recording button 7 after completion of fluoroscopic imaging. Accordingly, the fluoroscopic images 201 can be easily recorded as a still image or a moving image in the storage 6 both during fluoroscopic imaging and after completion of fluoroscopic imaging simply by operating the fluoroscopic recording button 7.

According to an embodiment, as described above, the fluoroscopic recording button 7 includes two buttons, the still image fluoroscopic recording button 71 that the operator operates to record the fluoroscopic image 201 as a still image in the storage 6, and the moving image fluoroscopic recording button 72 that the operator operates to record the fluoroscopic images 201 as a moving image in the storage 6. Accordingly, a still image recording button (still image fluoroscopic recording button 71) and a moving image recording button (moving image fluoroscopic recording button 72) are provided separately, and thus the operator can easily and separately perform an operation for recording a still image and an operation for recording a movie image. Consequently, it is possible to easily significantly reduce or prevent erroneous recording of a moving image in the case of intending to record a still image or erroneous recording of a still image in the case of intending to record a moving image.

According to an embodiment, as described above, the X-ray fluoroscopic imaging apparatus 100 is configured to record, as a still image in the storage 6, the arbitrary fluoroscopic image 201 being displayed on the display 3 when the fluoroscopic recording button 7 is operated while the arbitrary fluoroscopic image 201 among the fluoroscopic images 201 recorded in the temporary storage 5 is displayed on the display 3 after completion of fluoroscopic imaging. Accordingly, unlike the case in which only the fluoroscopic image 201 of a specific frame such as the final frame can be recorded as a still image after completion of fluoroscopic imaging, a desired fluoroscopic image 201 selected arbitrarily (freely) can be recorded as a still image in the storage 6 after completion of fluoroscopic imaging. Furthermore, unlike the case in which a desired fluoroscopic image 201 as a still image is recorded in the storage 6 during fluoroscopic imaging, it is not necessary to determine the timing for recording the fluoroscopic image 201. Consequently, even during fluoroscopic imaging in which it is difficult to determine the timing for recording the fluoroscopic image 201 as a still image during fluoroscopic imaging because of the short imaging time, such as fluoroscopic imaging for a newborn, a desired fluoroscopic image 201 can be easily recorded as a still image in the storage 6.

According to an embodiment, as described above, the X-ray fluoroscopic imaging apparatus 100 includes the reproduction and stop operation button 8 that the operator operates to reproduce or stop reproducing the fluoroscopic images 201 recorded in the temporary storage 5 on the display 3 after completion of fluoroscopic imaging. Furthermore, the X-ray fluoroscopic imaging apparatus 100 is configured to record, as a still image in the storage 6, the arbitrary fluoroscopic image 201 being displayed on the display 3 when the fluoroscopic recording button 7 is operated while the arbitrary fluoroscopic image 201 is displayed on the display 3 by the operation of the reproduction and stop operation button 8 after completion of fluoroscopic imaging. Accordingly, after completion of fluoroscopic imaging, an operation for arbitrarily selecting a desired fluoroscopic image 201 as a still image can be easily performed by the reproduction and stop operation button 8. Consequently, a desired fluoroscopic image 201 arbitrarily selected can be recorded as a still image in the storage 6 while an operation for selecting the desired fluoroscopic image 201 as a still image is easily performed.

According to an embodiment, as described above, the X-ray fluoroscopic imaging apparatus 100 is configured to record, as a still image in the storage 6, the fluoroscopic image 201 being displayed on the display 3 when the fluoroscopic recording button 7 is operated while the fluoroscopic image 201 acquired by the imager 1 is displayed on the display 3 in real time during fluoroscopic imaging. Accordingly, a desired fluoroscopic image 201 can be recorded as a still image in the storage 6 simply by operating the fluoroscopic recording button 7 at the timing when the desired fluoroscopic image 201 is displayed on the display 3 during fluoroscopic imaging. Consequently, the desired fluoroscopic image 201 as a still image can be easily and reliably recorded in the storage 6 during fluoroscopic imaging.

According to an embodiment, as described above, the X-ray fluoroscopic imaging apparatus 100 is configured to record, as a moving image in the storage 6, the images in the predetermined range 202 among the fluoroscopic images 201 recorded in the temporary storage 5 when the fluoroscopic recording button 7 is operated after completion of fluoroscopic imaging. Accordingly, the fluoroscopic images 201 in the predetermined range 202 can be recorded as a moving image in the storage 6 simply by operating the fluoroscopic recording button 7 after completion of fluoroscopic imaging. Consequently, desired fluoroscopic images 201 as a moving image can be easily and reliably recorded in the storage 6 after completion of fluoroscopic imaging. Furthermore, unlike the case in which the desired fluoroscopic images 201 as a moving image are recorded in the storage 6 during fluoroscopic imaging, it is not necessary to determine the timing for recording the fluoroscopic images 201 during fluoroscopic imaging. Consequently, unlike the case in which the timing for recording the fluoroscopic images 201 as a moving image is determined during fluoroscopic imaging, it is not necessary to record the fluoroscopic images 201 in a slightly longer time in consideration of recording omission. Thus, the recording time of the fluoroscopic images 201 can be easily reduced. As a result, the time required to record the fluoroscopic images 201 in the storage 6 can be reduced, and the data capacity of the storage 6 can be saved.

According to an embodiment, as described above, the X-ray fluoroscopic imaging apparatus 100 is configured to switchably enable or disable the auto fluoroscopic recording setting. Furthermore, the X-ray fluoroscopic imaging apparatus 100 is configured to record all of the fluoroscopic images 201 acquired by the imager 1 during fluoroscopic imaging in the storage 6 regardless of the operation of the fluoroscopic recording button 7 when the auto fluoroscopic recording setting is enabled. Accordingly, when the auto fluoroscopic recording setting is enabled, all of the fluoroscopic images 201 acquired by the imager 1 during fluoroscopic imaging can be recorded in the storage 6 even if the operation of the fluoroscopic recording button 7 is forgotten. Consequently, the risk that the fluoroscopic images 201 are not recorded in the storage 6 due to forgetting to operate the fluoroscopic recording button 7 can be reduced. Thus, it is possible to significantly reduce or prevent re-performing of fluoroscopic imaging of the subject 200 due to the fact that the fluoroscopic images 201 have not been recorded in the storage 6.

MODIFIED EXAMPLES

The embodiments disclosed this time must be considered as illustrative in all points and not restrictive. The scope of the present invention is not shown by the above description of the embodiments but by the scope of claims for patent, and all modifications (modified examples) within the meaning and scope equivalent to the scope of claims for patent are further included.

For example, while the fluoroscopic recording button includes two buttons, the still image fluoroscopic recording button and the moving image fluoroscopic recording button, in embodiments described above, the present invention is not limited to this. In the present invention, the fluoroscopic recording button may alternatively include one or three or more buttons.

For example, the fluoroscopic recording button may include one button that functions as the still image fluoroscopic recording button that the operator operates to record the fluoroscopic image as a still image in the storage, or the moving image fluoroscopic recording button that the operator operates to record the fluoroscopic images as a moving image in the storage due to a change in the length of the operation time. In this case, for example, when the fluoroscopic recording button is operated for a short time (first time), the fluoroscopic recording button may function as the still image fluoroscopic recording button, and when the fluoroscopic recording button is operated for a long time (second time longer than the first time), the fluoroscopic recording button may function as the moving image fluoroscopic recording button.

Alternatively, for example, the fluoroscopic recording button may include one button that functions as the still image fluoroscopic recording button that the operator operates to record the fluoroscopic image as a still image in the storage, or the moving image fluoroscopic recording button that the operator operates to record the fluoroscopic images as a moving image in the storage due to a change in the strength of the operating force. In this case, for example, when the fluoroscopic recording button is operated with a weak operating force (first operating force), the fluoroscopic recording button may function as the still image fluoroscopic recording button, and when the fluoroscopic recording button is operated with a strong operating force (second operating force stronger than the first operating force), the fluoroscopic recording button may function as the moving image fluoroscopic recording button. In other words, the fluoroscopic recording button may be a push-button type switch that can be pressed in two stages.

As described above, when the fluoroscopic recording button includes one button that functions as the still image fluoroscopic recording button or the moving image fluoroscopic recording button due to a change in the length of the operation time or the strength of the operating force, the number of fluoroscopic recording buttons can be reduced, and thus the structure of the X-ray fluoroscopic imaging apparatus can be simplified accordingly.

While the fluoroscopic recording button is a push-button type switch in embodiments described above, the present invention is not limited to this. In the present invention, the fluoroscopic recording button may alternatively be a touch-panel type switch.

While the X-ray fluoroscopic imaging apparatus includes the display in embodiments described above, the present invention is not limited to this. In the present invention, the X-ray fluoroscopic imaging apparatus may not necessarily include the display. In this case, the X-ray fluoroscopic imaging apparatus may be configured to output the fluoroscopic images to an external display and display the same on the external display.

While the X-ray fluoroscopic imaging apparatus is configured to record, as a moving image in the storage, the images in the predetermined range among the fluoroscopic images recorded in the temporary storage when the fluoroscopic recording button is operated after completion of fluoroscopic imaging in embodiments described above, the present invention is not limited to this. In the present invention, the X-ray fluoroscopic imaging apparatus may alternatively be configured to record, as a moving image in the storage, all of the fluoroscopic images recorded in the temporary storage when the fluoroscopic recording button is operated after completion of fluoroscopic imaging.

While the X-ray fluoroscopic imaging apparatus is configured to switchably enable or disable the auto fluoroscopic recording setting in embodiments described above, the present invention is not limited to this. In the present invention, the X-ray fluoroscopic imaging apparatus may not necessarily have the auto fluoroscopic recording setting.

Aspects

It will be appreciated by those skilled in the art that the exemplary embodiments described above are specific examples of the following aspects.

(Item 1)

An X-ray fluoroscopic imaging apparatus comprising:

an imager configured to perform fluoroscopic imaging of a subject with X-rays;

a temporary storage configured to temporarily record a fluoroscopic image acquired by the imager;

a storage configured to record, as a still image or a moving image, the fluoroscopic image recorded in the temporary storage; and a fluoroscopic recording button that an operator operates to record the fluoroscopic image as the still image or the moving image in the storage during the fluoroscopic imaging and record, as the still image or the moving image in the storage, the fluoroscopic image recorded in the temporary storage after completion of the fluoroscopic imaging.

(Item 2)

The X-ray fluoroscopic imaging apparatus according to item 1, wherein the X-ray fluoroscopic imaging apparatus is configured to record the fluoroscopic image as the still image or the moving image in the storage in accordance with operation of the fluoroscopic recording button during the fluoroscopic imaging, and record, as the still image or the moving image in the storage, the fluoroscopic image recorded in the temporary storage in accordance with the operation of the fluoroscopic recording button after the completion of the fluoroscopic imaging.

(Item 3)

The X-ray fluoroscopic imaging apparatus according to item 1 or 2, wherein the fluoroscopic recording button includes two buttons, a still image fluoroscopic recording button that the operator operates to record the fluoroscopic image as the still image in the storage, and a moving image fluoroscopic recording button that the operator operates to record the fluoroscopic image as the moving image in the storage.

(Item 4)

The X-ray fluoroscopic imaging apparatus according to item 1 or 2, wherein the fluoroscopic recording button includes one button configured to function as a still image fluoroscopic recording button that the operator operates to record the fluoroscopic image as the still image in the storage, or a moving image fluoroscopic recording button that the operator operates to record the fluoroscopic image as the moving image in the storage due to a change in a length of an operation time or a strength of an operating force.

(Item 5)

The X-ray fluoroscopic imaging apparatus according to any one of items 1 to 4, wherein the X-ray fluoroscopic imaging apparatus is configured to record, as the still image in the storage, an arbitrary fluoroscopic image being displayed on the display when the fluoroscopic recording button is operated while the arbitrary fluoroscopic image among fluoroscopic images recorded in the temporary storage is displayed on the display after the completion of the fluoroscopic imaging.

(Item 6)

The X-ray fluoroscopic imaging apparatus according to item 5, further comprising a reproduction and stop operation button that the operator operates to reproduce or stop reproducing the fluoroscopic images recorded in the temporary storage on the display after the completion of the fluoroscopic imaging; wherein the X-ray fluoroscopic imaging apparatus is configured to record, as the still image in the storage, the arbitrary fluoroscopic image being displayed on the display when the fluoroscopic recording button is operated while the arbitrary fluoroscopic image is displayed on the display by operation of the reproduction and stop operation button after the completion of the fluoroscopic imaging.

(Item 7)

The X-ray fluoroscopic imaging apparatus according to any one of items 1 to 6, wherein the X-ray fluoroscopic imaging apparatus is configured to record, as the still image in the storage, the fluoroscopic image being displayed on the display when the fluoroscopic recording button is operated while the fluoroscopic image acquired by the imager is displayed on the display in real time during the fluoroscopic imaging.

(Item 8)

The X-ray fluoroscopic imaging apparatus according to any one of items 1 to 7, wherein the X-ray fluoroscopic imaging apparatus is configured to record, as the moving image in the storage, images in a predetermined range among fluoroscopic images recorded in the temporary storage when the fluoroscopic recording button is operated after the completion of the fluoroscopic imaging.

(Item 9)

The X-ray fluoroscopic imaging apparatus according to any one of items 1 to 8, wherein the X-ray fluoroscopic imaging apparatus is configured to switchably enable or disable auto fluoroscopic recording setting; and the X-ray fluoroscopic imaging apparatus is configured to record all of fluoroscopic images acquired by the imager during the fluoroscopic imaging in the storage regardless of operation of the fluoroscopic recording button when the auto fluoroscopic recording setting is enabled.

What is claimed is:

1. An X-ray fluoroscopic imaging apparatus, comprising:
    an imager configured to perform fluoroscopic imaging of a subject with X-rays;
    a temporary storage configured to temporarily record a fluoroscopic image acquired by the imager;
    a storage configured to record, as a still image or a moving image, the fluoroscopic image recorded in the temporary storage;
    a fluoroscopic recording button and a reproduction and stop operation button that an operator operates to reproduce or stop reproducing fluoroscopic images recorded in the temporary storage on a display after the completion of the fluoroscopic imaging; and
    wherein the X-ray fluoroscopic imaging apparatus is configured to record, as the still image in the storage, an arbitrary fluoroscopic image being displayed on the display when the fluoroscopic recording button is operated while the arbitrary fluoroscopic image is displayed on the display by operation of the reproduction and stop operation button after the completion of the fluoroscopic imaging.

2. The X-ray fluoroscopic imaging apparatus, according to claim 1, wherein:
    the X-ray fluoroscopic imaging apparatus is configured to record the fluoroscopic image as the still image or the moving image in the storage in accordance with operation of the fluoroscopic recording button during the fluoroscopic imaging, and record, as the still image or the moving image in the storage, the fluoroscopic image recorded in the temporary storage in accordance with the operation of the fluoroscopic recording button after the completion of the fluoroscopic imaging.

3. The X-ray fluoroscopic imaging apparatus, according to claim 1, wherein:
    the fluoroscopic recording button includes two buttons, a still image fluoroscopic recording button that the operator operates to record the fluoroscopic image as the still image in the storage, and a moving image fluoroscopic recording button that the operator operates to record the fluoroscopic image as the moving image in the storage.

4. The X-ray fluoroscopic imaging apparatus, according to claim 1, wherein:
    the fluoroscopic recording button includes one button configured to function as a still image fluoroscopic recording button that the operator operates to record the fluoroscopic image as the still image in the storage, or a moving image fluoroscopic recording button that the operator operates to record the fluoroscopic image as the moving image in the storage due to a change in a length of an operation time or a strength of an operating force.

5. The X-ray fluoroscopic imaging apparatus, according to claim 1, wherein:
the X-ray fluoroscopic imaging apparatus is configured to record, as the still image in the storage, the fluoroscopic image being displayed on the display when the fluoroscopic recording button is operated while the fluoroscopic image acquired by the imager is displayed on the display in real time during the fluoroscopic imaging.

6. The X-ray fluoroscopic imaging apparatus, according to claim 1, wherein:
the X-ray fluoroscopic imaging apparatus is configured to record, as the moving image in the storage, images in a predetermined range among fluoroscopic images recorded in the temporary storage when the fluoroscopic recording button is operated after the completion of the fluoroscopic imaging.

7. The X-ray fluoroscopic imaging apparatus, according to claim 1, wherein:
the X-ray fluoroscopic imaging apparatus is configured to switchably enable or disable auto fluoroscopic recording setting; and
the X-ray fluoroscopic imaging apparatus is configured to record all of the fluoroscopic images acquired by the imager during the fluoroscopic imaging in the storage regardless of operation of the fluoroscopic recording button when the auto fluoroscopic recording setting is enabled.

8. An X-ray fluoroscopic imaging apparatus, comprising:
an imager configured to perform fluoroscopic imaging of a subject with X-rays;
a temporary storage configured to temporarily record a fluoroscopic image acquired by the imager;
a storage configured to record, as a still image or a moving image, the fluoroscopic image recorded in the temporary storage;
a fluoroscopic recording button that an operator operates to record the fluoroscopic image as the still image or the moving image in the storage during the fluoroscopic imaging and record, as the still image or the moving image in the storage, the fluoroscopic image recorded in the temporary storage after completion of the fluoroscopic imaging;
the X-ray fluoroscopic imaging apparatus is configured to record, as the still image in the storage, an arbitrary fluoroscopic image being displayed on a display when the fluoroscopic recording button is operated while the arbitrary fluoroscopic image among fluoroscopic images recorded in the temporary storage is displayed on the display after the completion of the fluoroscopic imaging;
a reproduction and stop operation button that the operator operates to reproduce or stop reproducing the fluoroscopic images recorded in the temporary storage on the display after the completion of the fluoroscopic imaging; and
wherein the X-ray fluoroscopic imaging apparatus is configured to record, as the still image in the storage, the arbitrary fluoroscopic image being displayed on the display when the fluoroscopic recording button is operated while the arbitrary fluoroscopic image is displayed on the display by operation of the reproduction and stop operation button after the completion of the fluoroscopic imaging.

* * * * *